US00PP10575P

United States Patent [19]

Bak et al.

[11] Patent Number: Plant 10,575

[45] Date of Patent: Aug. 25, 1998

[54] GUZMANIA PLANT NAMED RUMBA

[75] Inventors: Gerardus J. Bak, Assendelft; Nicolaas D. Steur, Oude Niedorp; Elly Bak, Rijsenhout, all of Netherlands

[73] Assignee: Corn.Bak B.V., Assendelft, Netherlands

[21] Appl. No.: 813,179

[22] Filed: Mar. 7, 1997

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Guzmania named 'Rumba' characterized by a plant form that is funnel-form rosette; plant height of approximately 50 cm; linear-lanceolate leaves measuring 25–40 cm in length and 3–4 cm in width; leaf color upperside of R.H.S. 147A and underside of R.H.S 137A; primary bract color of R.H.S. 34A to R.H.S. 169A and top bract color of R.H.S. 17A.

1 Drawing Sheet

The present invention relates to a new and distinct cultivar of Guzmania that is an interspecific hybrid, hereinafter referred to by the cultivar name 'Rumba'.

BACKGROUND OF THE INVENTION

Guzmania are predominantly epiphytic with a few terrestrial species and are native to the tropics. For the most part species vary in diameter from 7 or 8 inches to 3 to 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period the central vase-like part of the leaf rosette is desirably filled with water.

Guzmania is native to tropical America. Leaves of Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

Methods for cultivation and crossing of Guzmania are well known. For a detailed discussion, reference is made to the following publications, which are incorporated herein by reference. Benzing, David H., *THE BIOLOGY OF THE BROMELIADS*, mad River Press, Inc., Eureka (1980); Zimmer, Karl, *BROMELIEN*, Verlag Paul Parey, Berlin (1986); and Rauh, Werner, *BROMELIEN*, Verlag Eugen Ulmer, Stuttgart (1981).

The new cultivar 'Rumba' is a product of a planned breeding program and was originated by the inventors from a cross made during such a program in Assendelft, The Netherlands, in 1987. The male or pollen parent was a proprietary selection of *Guzmania wittmackii minor* identified by Code No. 8705260. The female or seed parent was a proprietary selection of *Guzmania lingulata minor* identified by Code No. 8705211.

The selection comprising the new variety was chosen from among progeny of the above cross following commencement of flowering in 1989 in Assendelft, The Netherland. The selection was first asexually propagated through off-shoots by, or under the supervision of, the inventors in Assendelft, with subsequent asexual reproduction through tissue culture. Continuous asexual propagation has demonstrated that the combination of characteristics as herein disclosed for the new cultivar 'Ruma', as observed in Assendelft, the Netherlands, are firmly fixed and are retained through successive generations of asexual reproduction.

'Rumba' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar. In comparision to the cultivar 'Samba', the cultivar, 'Rumba' produces an orange inflorescence.

BRIEF SUMMARY OF THE INVENTION

'Rumba' is particularly characterized by the following characteristics:

1. Plant form that is a funnel shaped rosette,
2. Plant height of approximately 50 cm,
3. Linear lanceolate leaves measuring 25–40 cm in length and 3–4 cm in width,
4. Leaf color upper side of R.H.S 147A and underside of R.H.S. 137A,
5. Primary bract color between R.H.S. 34A and R.H.S. 169A,
6. Top bract color of R.H.S. 17A.

BRIEF DESCRIPTION OF THE DRAWING

In the accompanying color photographic drawing, sheet 1 is a side view of a specimen of 'Rumba' showing the primary and top bracts.

DETAILED BOTANICAL DESCRIPTION

The following traits have been repeatedly observed and in combination distinguish 'Rumba' as a new and distinct cultivar. These observations, measurements and descriptions were taken for 'Rumba' plants grown under the following greenhouse conditions in Assendelft, The Netherlands. The minimum day and night temperature was 20° and 18° C., respectively. The ventilation temperature was 24° C. and the maximum light intensity was 18000 Lux. Fertilizer concentration was 0.5 to 1 EC comprising N:P:K in the ratio of 1:0.25 to 0.5:2 to 3. In addition, 3% of the total amount of fertilizer was $MgSO_4$.

Frequency of fertilization varied depending on time of year and ranged from once per week to once per month. Fertilization was more frequent during the spring and smmer months. Following fertilization, the plants were rinsed with sufficient clean water to remove residual fertilizer from the leaves.

With regard to induction of flowering, acetylene gas is allowed to bubble through 100 L of cool water for 30 min at a pressure of 0.5 bar. Whole plants are then sprayed with the acetylene solution making certain that the cup (vase) is filled. Spraying is done in the morning because the plants need light after this treatment and the plants are not watered again for at least two days. The plants are treated again, following this same protocol, one week later. Plants should not be fertilized for two to three weeks following treatment with acetylene because it is likely the flowers will not from and the bracts will remain green.

Plant:

*Form.*—Funnel form rosette.

*Height.*—Approximately 50 cm high when flowering.

*Growth habit.*—Stemless.

*Diameter.*—Approximately 60 cm.

Foliage:

*Size of leaf.*—Length approximately 25–40 cm and width approximately 3–4 cm.

*Shape of leaf.*—Linear-lanceolate.

*Surface texture.*—Smooth.

*Color.*—Upperside 147A R.H.S. Underside 137A R.H.S.

Bracts:

*Length.*—Scape bracts range from approximately 30 cm at the bottom of plant to approximately 15 cm just below the primary bracts. Primary bracts range from approximately 15 cm. to approximately 6 cm at the top of the plant.

*Width.*—Scape bracts are approximately 3.0 to 3.5 cm; and primary bracts are approximately 3.0 to 3.5 cm wide.

*Number.*—Scape bracts number approximately 10 and primary bracts number approximately 14.

*General shape.*—Lanceolate.

*Texture.*—Smooth.

*Margin.*—Entire.

*Color.*—Majority of primary bracts are between 34A and 169A R.H.S.; top primary bract is approximately 17A R.H.S.

Flowers:

*Borne (stalks).*—Erect.

*Shape of inflorescence.*—Compound.

*Size of inflorescence on stalk.*—Approximately 16 cm high.

*Diameter of inflorescence.*—Approximately 20 cm.

*Individual petals.*—(Mostly disposed within the floral bracts hidden under the primary bracts.) Length: Approximately 6.5 cm. Width: Approximately 0.5 cm. Quantity: Approximately 80 flowers spread over approximately 12 branches depending on the size of the plant. Color: 17A R.H.S.

*Time of blooming.*—A fully grown plant can bloom the whole year beginning approximately 11 weeks after induction through treatment with acetylene.

*Duration of blooms.*—Each flower blooms for 1 day and the total period of blooming following first bloom is about 5 weeks.

Reproductive organs:

*Ovaries.*—Superior.

*Stamens.*—6.

*Seed characteristics.*—Sterile hybrid and therefore no frit or seed is produced.

I claim:

1. A new and distinct cultivar of Guzmania plant named 'Rumba', as illustrated and described.

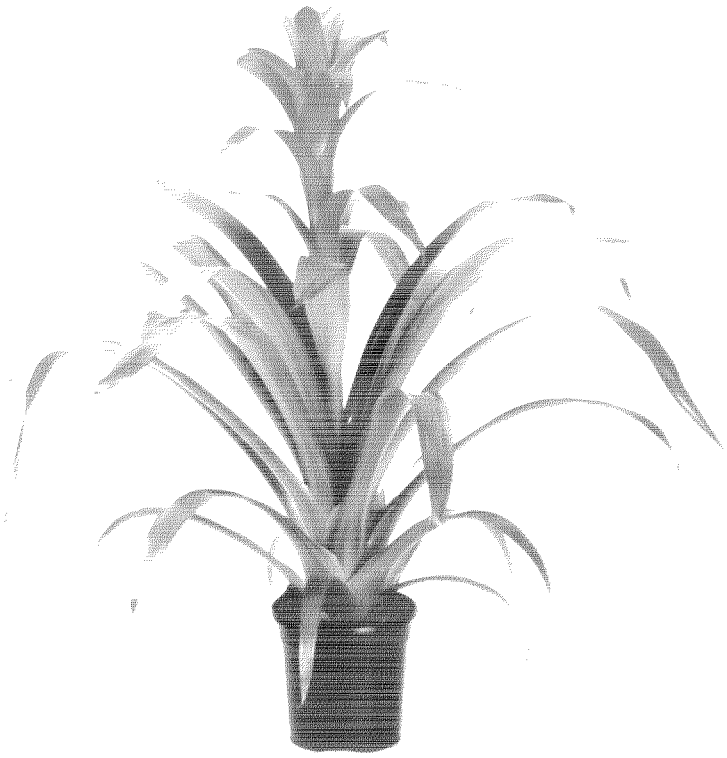

* * * * *